United States Patent [19]
Ulrich et al.

[11] Patent Number: 5,460,613
[45] Date of Patent: * Oct. 24, 1995

[54] SUCTION CATHETER ASSEMBLIES

[75] Inventors: Karl Ulrich, Belmont; Thomas Devlin, Cambridge, both of Mass.

[73] Assignee: Smiths Industries Medical Systems, Inc., Keene, N.H.

[*] Notice: The portion of the term of this patent subsequent to Sep. 27, 2011 has been disclaimed.

[21] Appl. No.: 213,827

[22] Filed: Mar. 14, 1994

Related U.S. Application Data

[63] Continuation of Ser. No. 967,844, Oct. 29, 1992, abandoned.

[51] Int. Cl.⁶ .......................... A61M 1/00; A61M 16/04
[52] U.S. Cl. ............... 604/118; 128/207.16; 128/207.14; 604/35
[58] Field of Search .................... 128/911, 912, 128/200.26, 205.24, 205.19, DIG. 29, 207.14–207.16; 604/35, 36, 163, 171, 250, 118

[56] References Cited

U.S. PATENT DOCUMENTS

| | | |
|---|---|---|
| 3,794,043 | 2/1974 | McGinnis . |
| 3,991,762 | 11/1976 | Radford . |
| 4,342,315 | 8/1982 | Jackson . |
| 4,351,328 | 9/1982 | Bodai . |
| 4,416,273 | 11/1983 | Grimes . |
| 4,515,592 | 5/1985 | Frankhouser . |
| 4,691,702 | 9/1987 | Chantzis . |
| 4,805,611 | 2/1989 | Hodgkins . |
| 4,834,710 | 5/1989 | Fleck . |
| 4,850,350 | 7/1989 | Jackson . |
| 4,874,364 | 10/1989 | Morris et al. . |
| 4,875,718 | 10/1989 | Marten . |
| 5,083,561 | 1/1992 | Russo . |
| 5,088,486 | 2/1992 | Jinotti . |
| 5,125,893 | 6/1992 | Dryden . |
| 5,139,018 | 8/1992 | Brodsky et al. . |
| 5,140,983 | 8/1992 | Jinotti . |
| 5,158,569 | 10/1992 | Strickland . |
| 5,349,950 | 9/1994 | Ulrich et al. ............ 128/207.14 |

*Primary Examiner*—Randall L. Green
*Assistant Examiner*—Rob Clarke
*Attorney, Agent, or Firm*—Pollock, Vande Sande & Priddy

[57] ABSTRACT

A suction catheter assembly has an aspirating catheter that is enclosed along its length within a protective sleeve. The catheter extends from a vacuum connecting member, which can be connected to a suction source, and a patient connecting member which has a coupling for connection to a tracheal tube and two side ports for connection to ventilation equipment. A one-way valve in the patient connecting member forms a sliding seal with the catheter and allows trapped gas in the sleeve to escape into the patient connecting member when the catheter is advanced.

13 Claims, 4 Drawing Sheets

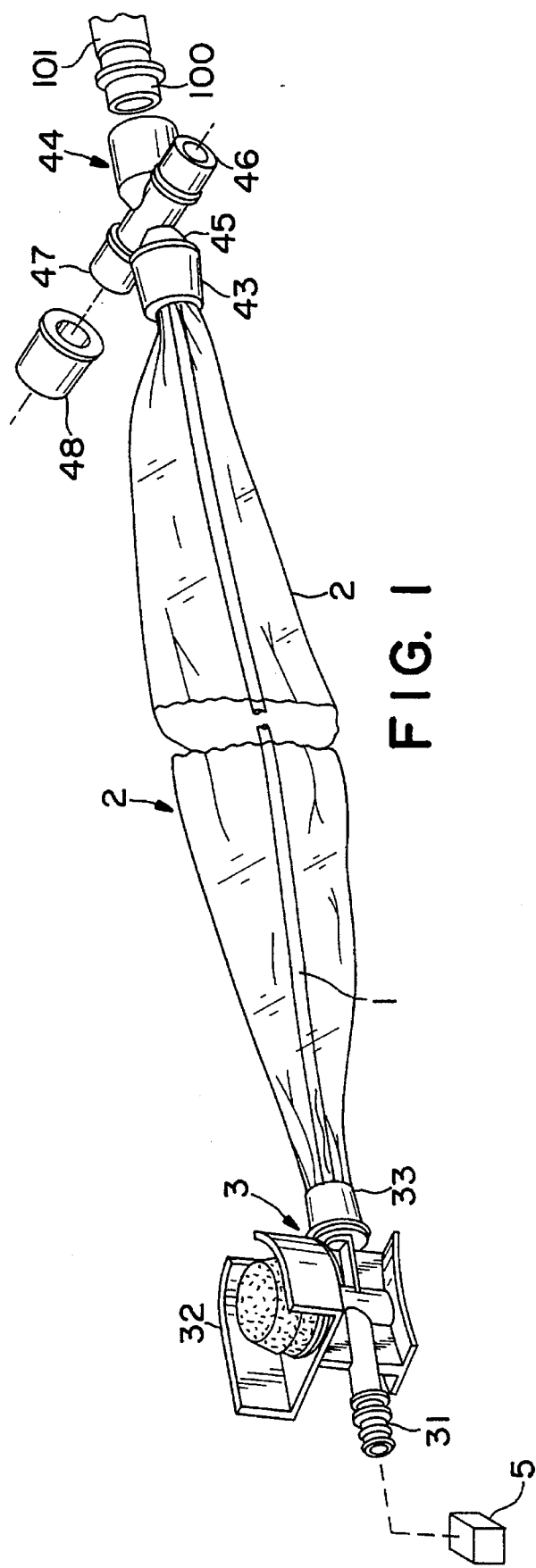
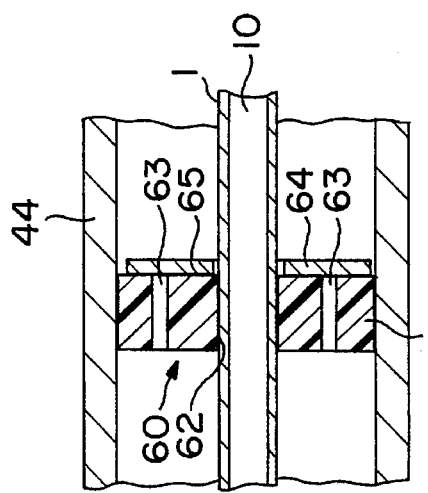
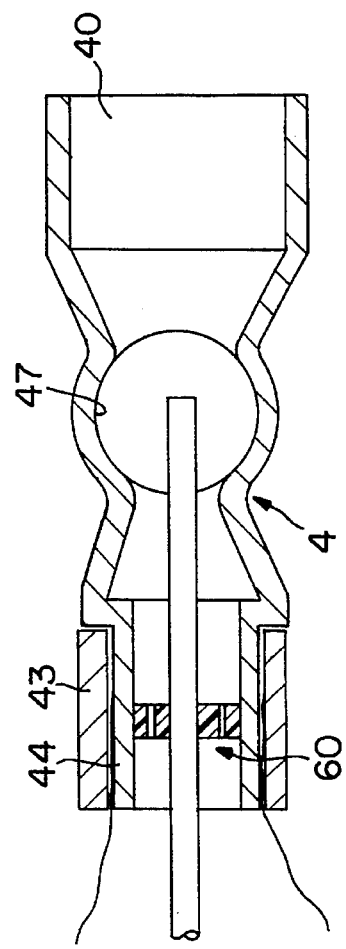
FIG. 1
FIG. 4
FIG. 5

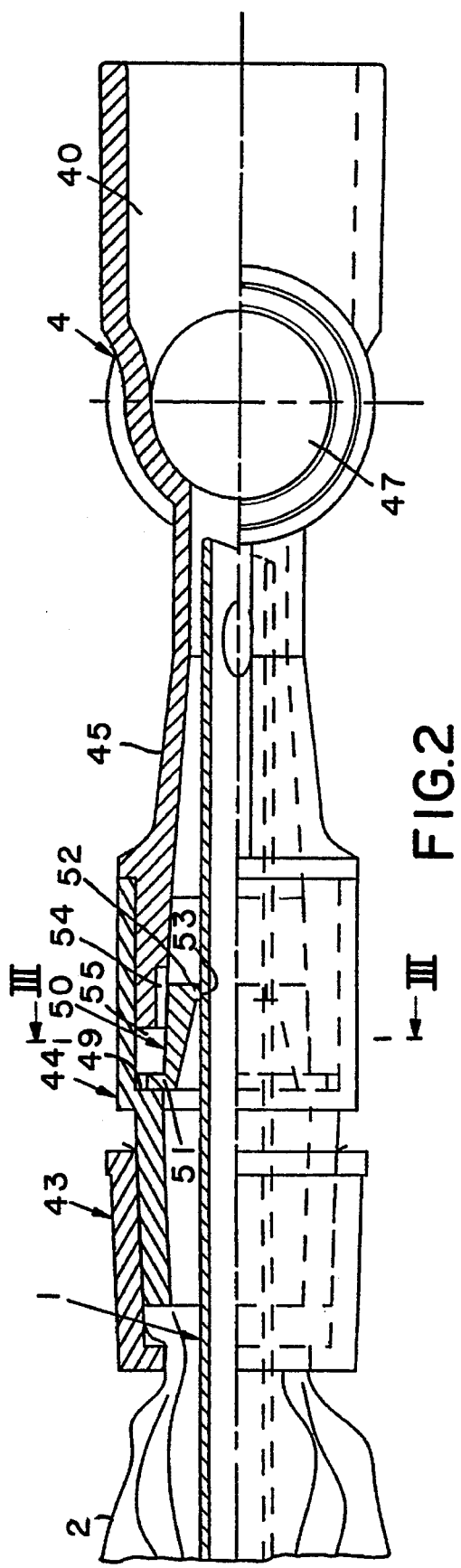
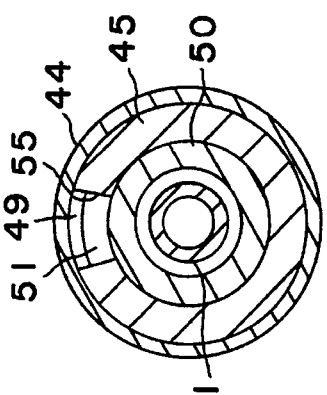
FIG.2
FIG.3

SUCTION CATHETER ASSEMBLIES

This application is a continuation of Ser. No. 07/967,844 filed on Oct. 28, 1992, now abandoned.

BACKGROUND OF THE INVENTION

This invention relates to suction catheter assemblies.

The invention is more particularly concerned with assemblies of the kind having an aspirating catheter enclosed within a protective, flexible sleeve and which can be advanced through a coupling at one end of the assembly. The coupling has one port connected to a tracheal tube and two further side ports by which ventilation of the patient can take place. In use, the machine end of the catheter is connected to a suction source via a valve. Secretions that build up on the inside of the tracheal tube, the trachea and bronchi can be periodically removed by opening the valve and advancing the catheter through the coupling and down the tracheal tube. The coupling enables ventilation of the patient to continue while suctioning takes place.

One problem with this kind of assembly is that air may enter the sleeve causing it to inflate which can make subsequent use of the assembly more difficult. A small amount of air will be present in the sleeve as a result of assembly and additional air can be pulled into the sleeve during the negative pressure cycle of sterilization. Air from the ventilation system, during use, can also be forced back into the sleeve. Although a sliding seal can be provided in the coupling with the outside of the catheter, this does not provide a total air seal. Attempts to improve the seal by making it a tighter fit tend to cause an indentation in the catheter, especially when it is stored for prolonged periods or subjected to elevated temperature, such as during sterilization. One way of preventing the accumulation of air in the sleeve is to provide a small vent that allows air to escape to atmosphere. This, however, is not desirable because it can allow the escape of contaminated material from the assembly onto the user.

Examples of catheter assemblies having an aspirating catheter which is contained within a sleeve and which can be pushed through a sliding seal on a coupling are described in several patents, such as U.S. Pat. No. 3,991,762 to Radford; U.S. Pat. No. 4,569,344 to Palmer; U.S. Pat. No. 4,638,539 to Palmer; U.S. Pat. No. 4,696,296 to Palmer; U.S. Pat. No. 4,825,859 to Lambert; U.S. Pat. No. 4,834,726 to Lambert; U.S. Pat. No. 4,836,199 to Palmer;U.S. Pat. No. 4,838,255 to Lambert; U.S. Pat. No. 4,872,579 to Palmer; U.S. Pat. No. 4,938,741 to Lambert; U.S. Pat. No. 4,967,743 to Lambert; U.S. Pat. No. 4,981,466 to Lambert; U.S. Pat. No. 5,025,806 to Palmer; U.S. Pat. No. 5,029,580 to Radford; U.S. Pat. No. 5,060,646 to Page; U.S. Pat. No. 5,065,754 to Jensen; U.S. Pat. No. 5,073,164 to Hollister; and GB 2207736 to Hollister. Suction catheter assemblies of this kind are also available from Smiths Industries Medical Systems Inc under the trade mark STERICATH and from Ballard Medical Products Inc under the trade mark TRACHCARE.

SUMMARY OF THE INVENTION

It is an object of the present invention to provide a suction catheter assembly in which there is a reduced risk of inflation of the sleeve and in which the user is protected from contact with contaminated material.

According to one aspect of the present invention there is provided a suction catheter assembly for use in removing undesirable fluid from a patient, the catheter assembly comprising: an aspirating catheter having a proximal end and a distal end, said distal end being suitable for insertion into a patient; a vacuum connecting member located in the vicinity of the proximal end of the aspirating catheter; a patient connecting member mounted to surround the aspirating catheter in the vicinity of the distal end of the aspirating catheter, the patient connecting member having a sliding seal with the outside of the aspirating catheter; a protective sleeve surrounding at least the majority of the length of the catheter and extending between the vacuum connecting member and the patient connecting member, the protective sleeve being adapted to permit the distal end of the catheter to be extended from the protective sleeve into the patient and to be withdrawn from the patient; and one way valve means within the patient connecting member, the one-way valve means permitting gas flow through it out of the interior of the sleeve and into the patient connecting member but preventing any substantial gas flow through the valve member into the sleeve such that any gas trapped in the sleeve can escape into the patient connecting member through the one-way means.

The one-way valve means may take various different forms. In one form, the sliding seal and one-way valve means are provided by a resilient tubular member having a flange at its proximal end and an internal wiper seal with the catheter at its distal end, the flange having a proximal surface and a distal surface, the assembly including a shoulder that faces distally of the assembly, the proximal surface of the flange lying against the shoulder and the distal surface of the flange being exposed to gas pressure in the patient connecting member distally of the one-way valve means such that the flange is forced into closer contact with the shoulder by gas pressure on the distal side of the one-way valve means and is lifted away from the shoulder by gas pressure on the proximal side of the one-way valve means. The tubular member may have a wall that increases in thickness towards its distal end.

Alternatively, the one-way valve means may have a disc with a central aperture through which the catheter extends and makes a sliding seal. The disc preferably has at least one peripheral aperture therethrough, and a displaceable member such as a flexible diaphragm which overlies a distal face of the disc in the region of the said peripheral aperture such that gas pressure on the proximal side of the disc is effective to displace the diaphragm away from the peripheral aperture so as to allow gas flow through the peripheral aperture.

In another form of assembly, the one-way valve means may include a porous disc with an aperture through which the catheter extends, and a flexible diaphragm which overlies a distal face of the disc such that gas pressure on the proximal side of the disc is effective to displace a part of the diaphragm away from the disc so as to allow gas flow therethrough, and such that gas pressure on the distal side of the disc is effective to urge the diaphragm against the disc and prevent any substantial gas flow therethrough.

According to another aspect of the present invention there is provided a method of suctioning undesirable fluid from a patient in which the patient connecting member on the assembly is connected to a tracheal tube and the vacuum connecting member is connected to a suction source. The patient is ventilated via the patient connecting member such that the one-way valve means prevents any substantial gas flow into the sleeve and the aspirating catheter is advanced through the sliding seal so as to aspirate the patient without interruption of ventilation and such that the one-way valve means allows any trapped air in the sleeve to be forced into the patient connecting member as the aspirating catheter is advanced. Subsequently, the aspirating catheter is withdrawn through the sliding seal.

Several suction catheter assemblies according to the present invention, will now be described, by way of example, with reference to the accompanying drawings.

BRIEF DESCRIPTION OF THE DRAWINGS

FIG. 1 is a perspective view of the assembly;

FIG. 2 is a sectional side elevation of the patient connecting member according to one embodiment of the present invention;

FIG. 3 is a transverse section along the line III—III of FIG. 2;

FIG. 4 is a sectional view of a second embodiment of the patient connecting member;

FIG. 5 is a sectional view of a third embodiment of the patient connecting member;

DESCRIPTION OF THE PREFERRED EMBODIMENTS

Figure 6:
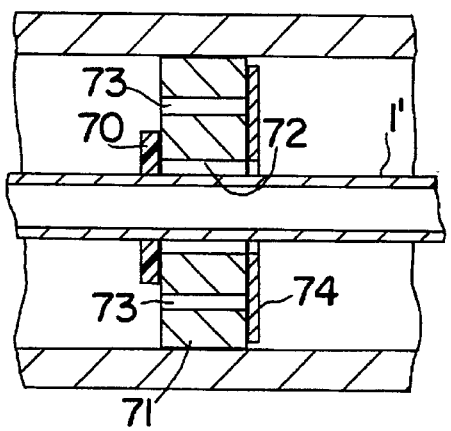
FIG. 6 is an enlarged sectional view of alternative valve

With reference first to FIGS. 1 to 3, the suction catheter assembly comprises an aspirating catheter 1 that extends within a flexible, protective sleeve 2 between a vacuum connecting member 3 and a patient connecting member 4.

The aspirating catheter 1 is of conventional construction having an outside diameter of about 4–5 mm arid a length of about 55 cm. In the illustrated example, the catheter 1 has a single lumen 10 although catheters with multiple lumens for use in irrigation and/or oxygen supply could be used. At its machine or proximal end, the catheter 1 is secured to the vacuum connecting member 3.

The vacuum connecting member 3 is molded from a rigid plastics material and has a bore (not shown) extending along it into one end of which the catheter 1 is bonded. The opposite end of the bore extends through a spigot 31 which, in use, is connected to tubing (not shown) extending to a vacuum or suction source 5. The vacuum connecting member 3 includes a conventional manually-operated valve 32 which normally prevents flow through the connecting member 3 and catheter 1 but which can be pressed down by the user to open the valve and connect the lumen 10 of the catheter to the suction source 5.

The proximal end of the sleeve 2 is secured to the vacuum connecting member 3 beneath a collar 33 secured to the distal end of the vacuum connecting member. The distal end of the sleeve 2 is similarly secured to the patient connecting member 4 by means of a collar 43 which is secured on a proximal extension piece 44 that is in turn joined to the main body 45 of the patient connecting member.

The patient connecting member 4 is of generally cruciform shape, having a female luer coupling 40 at its distal or patient end which is aligned with the axis of the member and with the proximal extension 44. The coupling 40 is adapted to be connected to a cooperating coupling (not shown) on the end of a tracheal tube. Two side ports 46 and 47 extend at right angles to the axis of the connecting member, directly opposite one another, about midway along the length of the connecting member. These two side ports 46 and 47 communicate directly with the interior of the coupling 40 and are used in the conventional manner to connect with ventilation apparatus. One port may be used for inhalation gas and the other port used for exhalation gas. Alternatively, one of the ports 47 may be closed by a cap 48 and inhalation and exhalation both be effected through the other port 46.

Within the patient connecting member 4 there is a novel sealing device and one-way valve 50. This takes the form of a resilient, generally tubular member which has a flexible, external, annular flange 51 at its proximal end that is trapped between the main body 45 and a shoulder 49 in the proximal extension piece 44. The shoulder 49 faces distally of the assembly and is contacted by the proximal surface of the flange 51. The proximal end of the main body 45 has one or more cut-away portions 55 so that the flange 51 can be lifted away from the shoulder 49, into these portions, by elevated gas pressure on the proximal side of the flange. At its distal end, the valve 50 has an internally-extending wiper seal 52 defining a circular aperture 53 through which the catheter 1 extends and to which a sliding seal is formed. Externally, the valve 50 has a shallow taper of about 2°–3°, so that it has a smaller diameter at its distal end. The distal surface of the flange 51 is exposed to gas pressure on the distal side of the valve by means of the cut-away portions 55 and passages 54 formed around the inside of the proximal end of the main body 45 of the patient connecting member. Internally, the valve 50 has a steeper taper of about 13°–14° so that it has a smaller internal diameter and a greater wall thickness at its distal end. The interior of the valve 50 is exposed to gas pressure on the proximal side of the valve.

In operation, the coupling 40 of the connecting member 4 is secured to a coupling 100 on the end of a tracheal tube 101 and its side ports 46 and 47 are connected to a ventilator. The vacuum coupling member 3 is connected to the suction source 5 but, as long as the manual valve 32 remains unactuated, no suction is applied to the catheter 1. While mechanical ventilation takes place, there is raised, positive pressure within the patient connecting member 4 (on the distal side of the valve 50) which forces the distal side of the flange 51 against the shoulder 49, thereby improving the seal of the flange on the shoulder and blocking gas flow into the sleeve 2.

When aspiration of fluid from the trachea or bronchi is required, the user grips the catheter 1 through the sleeve 2 and pushes it forwardly so that the distal, patient end of the catheter is advanced through the connecting member 4 and into the tracheal tube 101. When the catheter 1 has been inserted to the desired depth, the user depresses the valve 32 so that the catheter is connected to the suction source 5 and fluid in the vicinity of the tip of the catheter is sucked into the catheter and removed. During aspiration, ventilation of the patient occurs normally. When aspiration is complete, the catheter 1 is pulled back into the sleeve 2, the assembly remaining attached to the tracheal tube connector 100 so that it can be reused when necessary.

Although the sliding seal of the valve 50 with the catheter 1 is effective to prevent any significant flow of gas into the sleeve 2, there may be some seepage of gas around the catheter, especially when the catheter is being manipulated during aspiration. The valve 50 is, however, effective to allow any gas trapped inside the sleeve 2 to escape when pressure on its proximal side exceeds that on the distal side. The action of gripping the sleeve 2 and advancing the catheter 1 has the effect of compressing any trapped gas in the sleeve, thereby increasing its pressure and allowing it to open the valve by forcing the flange 51 away from the shoulder 49 in the cut-away portions 55. The valve 50, therefore, acts as a one-way valve, allowing flow only distally of the valve. In this way, build-up of gas in the sleeve 2 is prevented since the sleeve 2 can vent at relatively low pressure. Because the venting occurs into the connecting member 4, the vented gas is carried to the ventilation system without any risk of cross contamination to the clinician.

Various modifications are possible to the embodiment described. For example, the valve could be of the form shown in FIGS. 4 and 5. In this arrangement, the sealing device and one-way valve 60 takes the form of a disc 61 of a stiff but resilient material, such as a plastics, which is about 5 mm thick and is bonded to the inside of the connecting member within the proximal extension 44 or at some other point proximally of the ventilation side ports 46 and 47. The disc 61 has a circular central aperture 62 which is a close sliding fit about the outside of the catheter 1 so as to form a sliding seal with its surface. The disc 61 is also provided with several smaller peripheral apertures 63 which extend through its thickness. The sealing device 60 is completed by a displaceable member in the form of a thin annular diaphragm 64 of a flexible gas-impervious plastics material. The diaphragm 64 is slightly smaller in external diameter than the disc 61 and has a central aperture that is slightly larger than the aperture 62 of the disc. The diaphragm 64 is bonded, such as by welding, solvent or adhesive, around its central aperture to the distal face of the disc 61 to form an annular bond 65. Outwardly of this bond 65, the diaphragm 64 overlies the peripheral apertures 63 and is unattached to the disc 61. The nature of the diaphragm 64 is such that it will remain flat against the surface of the disc for any orientation of the assembly but it can be deflected readily away from the disc by positive gas pressure through the apertures 63.

The one-way valve 50 or 60 could be provided in one part of a patient connecting member, with the side ports 46 and 47 and the female luer coupling 40 being provided in a separate part that is coupled together with the first part during use.

The one-way valve and the sliding seal with the catheter could be formed by separate components, as shown in FIG. 6. In this arrangement, the sliding seal with the catheter 1' is provided by a gasket 70 secured to one side of a rigid valve disc 71. The valve disc 71 is similar to the disc 61 but has a larger central aperture 72 to allow freer movement of the catheter. A diaphragm 74 covers peripheral apertures 73 through the disc and seals them closed in the same way as described above.

Figure 7:
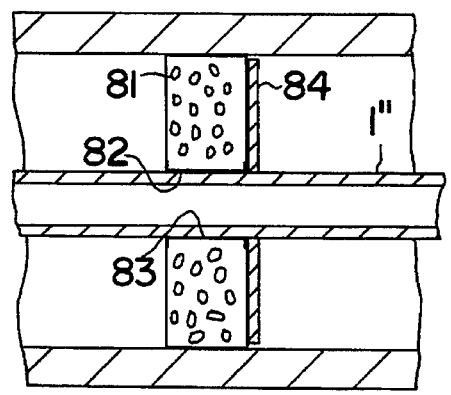
FIG. 7 is an enlarged sectional view of another alternative valve.

Another modification is shown in FIG. 7. In this, a disc 81 is made from a material that is porous through its thickness. A non-porous film 82 may be provided through a central aperture 83 to form an effective sliding seal with the catheter 1". A flexible annular diaphragm 84 is attached only around its inner edge to the distal face of the disc 81 so that gas can flow through the disc in the distal direction but is impeded in a proximal direction.

Figure 8:
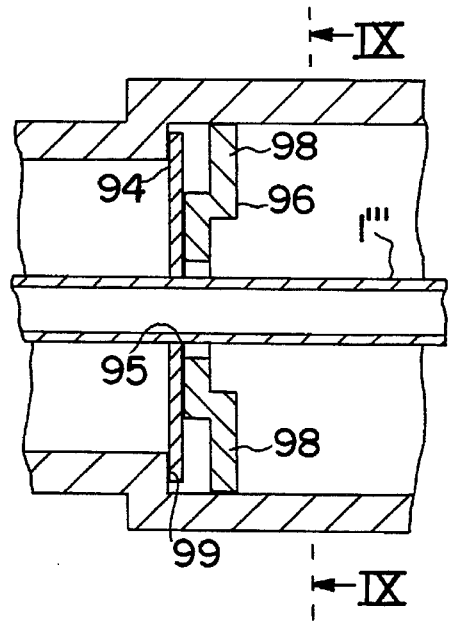
FIG. 8 is an enlarged sectional view of still another alternative valve.
Figure 9:
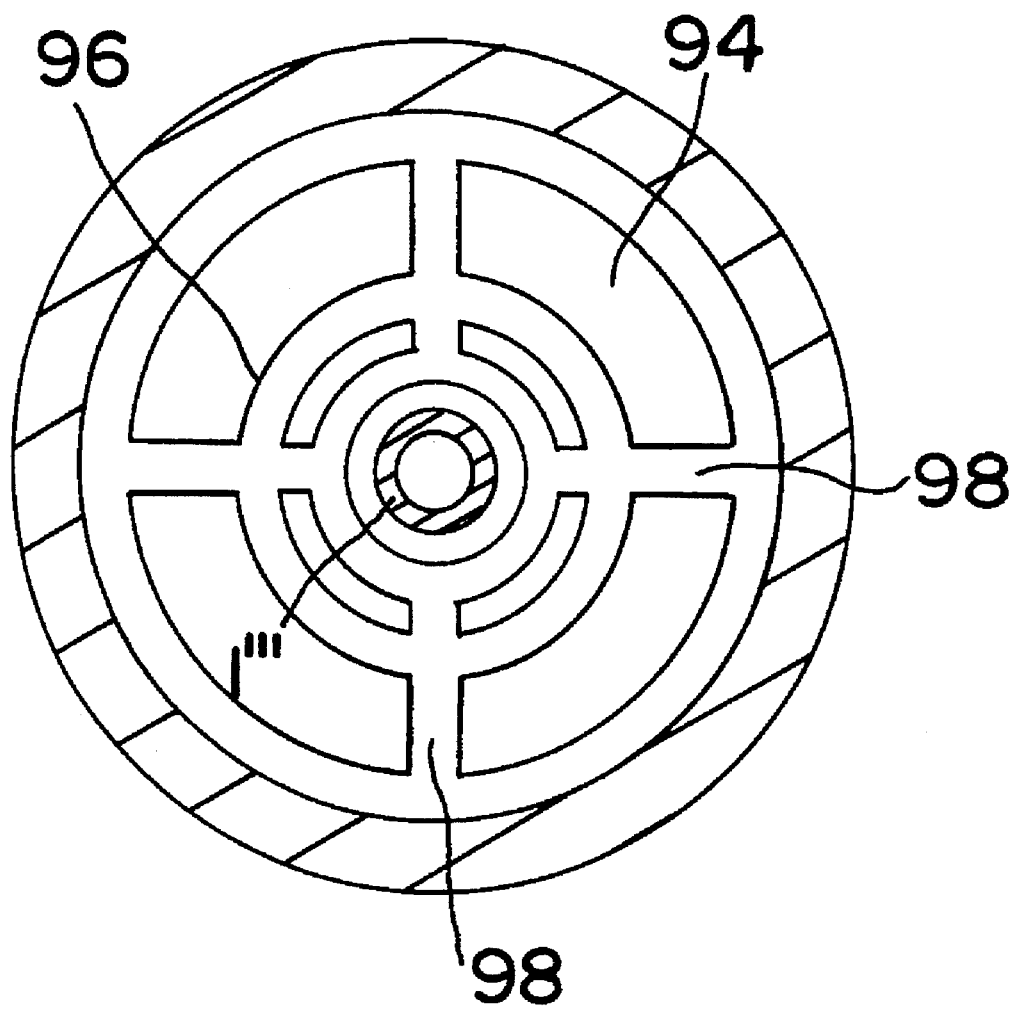
FIG. 9 is a transverse section along the line IX—IX of FIG. 8.

In the arrangement shown in FIGS. 8 and 9, a diaphragm 94 acts as both a valve member and as a sliding seal with the catheter 1'''. The diaphragm 94 has a central aperture 95 that is a sliding seal with the outside of the catheter; the diaphragm being supported centrally by a skeletal support 96 that is secured to the housing of the patient connecting member 4 by means of radially extending arms 98. An internal annular step 99 is formed around the inside of the housing, the step facing distally of the assembly and the outer peripheral region of the diaphragm 94 being seated on this step. The edge of the diaphragm 94 is deformed away from the step 99 by pressure from within the sleeve but, in normal use, the pressure from the respiration system forces the edge of the diaphragm in a proximal direction, more firmly against the step so that air can only flow in one direction.

We claim:

1. A suction catheter assembly for use in removing undesirable fluid from a patient, said catheter assembly comprising:

an aspirating catheter having a proximal end and a distal end, said distal end being suitable for insertion into a patient;

a vacuum connecting member located in the vicinity of the proximal end of the aspirating catheter;

a patient connecting member mounted to surround the aspirating catheter in the vicinity of the distal end of the aspirating catheter, wherein the patient connecting member has a sliding seal with the outside of the aspirating catheter;

a protective sleeve surrounding at least the majority of the length of the catheter and extending between said vacuum connecting member and said patient connecting member, wherein said protective sleeve is adapted to permit the distal end of said catheter to be extended from said protective sleeve into the patient and to be withdrawn from the patient; and one-way valve means Within the patient connecting member and separate from said Sliding seal, said one-way valve means for permitting gas flow through it from inside the sleeve and into the patient connecting member without passing through said sliding seal but preventing any substantial gas flow through the one-way valve means into the sleeve such that any gas trapped in the sleeve can escape into the patient connecting member through said one-way valve means, wherein the sliding seal and one-way valve means are provided by different parts of a resilient tubular member, said tubular member having a flange at its proximal end and an internal wiper seal with the catheter at its distal end, the flange having a proximal surface and a distal surface, wherein the assembly includes a shoulder that faces distally of the assembly, and wherein the proximal surface of the flange lies against the shoulder and the distal surface of the flange is exposed to gas pressure in the patient connecting member distally of the one-way valve means such that the flange is forced into closer contact with the shoulder by gas pressure on the distal side of the one-way valve means and is lifted away from the shoulder by gas pressure on the proximal side of the one-way valve means.

2. A suction catheter assembly according to claim 1, wherein the tubular member has a wall that increases in thickness towards its distal end.

3. A suction catheter assembly for use in removing undesirable fluid from a patient, said catheter assembly comprising:

an aspirating catheter having a proximal end and a distal end, said distal end being suitable for insertion into a patient;

a vacuum connecting member located in the vicinity of the proximal end of the aspirating catheter;

a patient connecting member mounted to surround the aspirating catheter in the vicinity of the distal end of the aspirating catheter, wherein the patient connecting member has a sliding seal with the outside of the aspireting catheter;

a protective sleeve surrounding at least the majority of the length of the catheter and extending between said vacuum connecting member and said patient connecting member, wherein said protective sleeve is adapted to permit the distal end of said catheter to be extended from said protective sleeve into the patient and to be withdrawn from the patient; and one-way valve means within the patient connecting member and separate from said sliding seal, said one-way valve means for permitting gas flow through it from inside the sleeve and into the patient connecting member without passing through said sliding seal but preventing any substantial gas flow through the one-way valve means into the sleeve such that any gas trapped in the sleeve can escape into the patient connecting member through said one-way valve means, wherein the patient connecting member includes a patient end coupling aligned with the aspirating catheter, wherein the patient end coupling is adapted to be coupled with a tracheal tube, and has two side ports which communicate with the interior of the patient end coupling on the distal side of the one-way valve means, and wherein the two side ports are adapted for connection to ventilation apparatus such that the patient can be aspirated without interruption of ventilation.

4. A suction catheter assembly according to claim 1, wherein the one-way valve means includes a disc with a central aperture through which the catheter extends, the disc having at least one peripheral aperture therethrough, and wherein the one-way valve means includes a displaceable member which overlies a distal face of the disc in the region of said peripheral aperture such that gas pressure on the proximal side of the disc is effective to displace the dispaceable member away from the peripheral aperture so as to allow gas flow through the peripheral aperture.

5. A suction catheter assembly according to claim 4, wherein the displaceable member is a flexible diaphragm.

6. A suction catheter assembly according to claim 5, wherein the said sliding seal is provided by contact of the central aperture through the disc with the surface of the catheter.

7. A suction catheter assembly according to claim 5, wherein the diaphragm is of annular shape, and wherein the diaphragm is bonded centrally to the disc.

8. A suction catheter assembly according to claim 7, wherein the said sliding seal is provided by contact of the central aperture through the disc with the surface of the catheter.

9. A suction catheter assembly according to claim 4, wherein the said sliding seal is provided by contact of the central aperture through the disc with the surface of the catheter.

10. A suction catheter assembly to claim 4, wherein said one-way valve means additionally includes a gasket, and wherein the gasket has an aperture that makes the said sliding seal with the catheter.

11. A suction catheter assembly for use in removing undesirable fluid from a patient, said catheter assembly comprising:

an aspirating catheter having a proximal end and a distal end, said distal and being suitable for insertion into a patient;

a vacuum connecting member located in the vicinity of the proximal end of the aspirating catheter;

a patient connecting member mounted to surround the aspirating catheter in the vicinity of the distal end of the aspirating catheter, wherein the patient connecting member has a sliding seal with the outside of the aspirating catheter, a protective sleeve surrounding at least the majority of the length of the catheter and extending between said vacuum connecting member and said patient connecting member, wherein said protective sleeve is adapted to permit the distal end of said catheter to be extended from said protective sleeve into the patient and to be withdrawn from the patient; and one-way valve means within the patient connecting member and separate from said sliding seal, said one-way valve means for permitting gas flow through it from inside the sleeve and into the patient connecting member without passing through said sliding seal but preventing any substantial gas flow through the one-way valve means into the sleeve such that any gas trapped in the sleeve can escape into the patient connecting member through said one-way valve means, wherein the vacuum connecting member includes a manually-operable valve, and wherein the manually-operable valve normally blocks fluid flow along the aspirating catheter but can be manually opened to permit fluid flow along the catheter.

12. A suction catheter assembly according to claim 11, wherein said one-way valve means includes a porous disc with an aperture through which the catheter extends, and a flexible diaphragm which overlies a distal face of the disc such that gas pressure on the proximal side of the disc is effective to displace a part of the diaphragm away from the disc so as to allow gas flow therethrough, and such that gas pressure on the distal side of the disc is effective to urge the diaphragm against the disc and prevent gas flow therethrough.

13. A suction catheter assembly according to claim 12, wherein the porous disc has a non-porous film through its aperture, and wherein the aperture makes a sliding seal with the catheter.

* * * * *